(12) United States Patent
Chen et al.

(10) Patent No.: US 9,957,477 B2
(45) Date of Patent: *May 1, 2018

(54) METHOD FOR ENZYMATIC TREATMENT OF TISSUE PRODUCTS

(71) Applicant: LifeCell Corporation, Branchburg, NJ (US)

(72) Inventors: Yi Chen, Lawrenceville, NJ (US); Hui Xu, Plainsboro, NJ (US); Li Ting Huang, Branchburg, NJ (US); Wenquan Sun, Warrington, PA (US); Hua Wan, Princeton, NJ (US)

(73) Assignee: LifeCell Corporation, Branchburg, NJ (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/962,125

(22) Filed: Dec. 8, 2015

(65) Prior Publication Data

US 2016/0090572 A1 Mar. 31, 2016

Related U.S. Application Data

(63) Continuation of application No. 14/019,274, filed on Sep. 5, 2013, now Pat. No. 9,238,793, which is a continuation-in-part of application No. 13/457,791, filed on Apr. 27, 2012, now Pat. No. 9,206,442.

(60) Provisional application No. 61/479,937, filed on Apr. 28, 2011.

(51) Int. Cl.
| | |
|---|---|
| *C12Q 1/02* | (2006.01) |
| *A61K 35/12* | (2015.01) |
| *C12N 5/00* | (2006.01) |
| *A61L 27/36* | (2006.01) |
| *A61L 27/56* | (2006.01) |

(52) U.S. Cl.
CPC ........ *C12N 5/0068* (2013.01); *A61L 27/3604* (2013.01); *A61L 27/3687* (2013.01); *A61L 27/56* (2013.01); *A61L 2430/40* (2013.01)

(58) Field of Classification Search
None
See application file for complete search history.

(56) References Cited

U.S. PATENT DOCUMENTS

| | | | |
|---|---|---|---|
| 4,098,571 A | 7/1978 | Miyata et al. | |
| 5,336,616 A | 8/1994 | Livesey et al. | |
| 5,364,756 A | 11/1994 | Livesey et al. | |
| 5,547,681 A | 8/1996 | Clark et al. | |
| 5,855,620 A | 1/1999 | Bishopric et al. | |
| 6,166,288 A | 12/2000 | Diamond et al. | |
| 6,267,786 B1 | 7/2001 | Stone | |
| 6,379,710 B1 | 4/2002 | Badylak | |
| 6,381,026 B1 | 4/2002 | Schiff et al. | |
| 6,455,309 B2 | 9/2002 | Stone | |
| 6,835,385 B2 | 12/2004 | Buck | |
| 6,933,326 B1 | 8/2005 | Griffey et al. | |
| 6,936,271 B1 | 8/2005 | Oliver et al. | |
| 7,358,284 B2 | 4/2008 | Griffey et al. | |
| 7,498,412 B2 | 3/2009 | Huang et al. | |
| 9,238,793 B2 | 1/2016 | Chen et al. | |
| 2002/0115208 A1 | 8/2002 | Mitchell et al. | |
| 2003/0035843 A1 | 2/2003 | Livesey et al. | |
| 2003/0068815 A1 | 4/2003 | Stone et al. | |
| 2003/0143207 A1 | 7/2003 | Livesey et al. | |
| 2004/0191226 A1 | 9/2004 | Badylak | |
| 2004/0234507 A1 | 11/2004 | Stone | |
| 2005/0028228 A1 | 2/2005 | McQuillan et al. | |
| 2005/0186286 A1* | 8/2005 | Takami .................. | A61K 35/36 424/572 |
| 2005/0260176 A1* | 11/2005 | Ayares ............... | A01K 67/0276 424/93.7 |
| 2006/0073592 A1 | 4/2006 | Sun et al. | |
| 2006/0127375 A1 | 6/2006 | Livesey et al. | |
| 2006/0210960 A1 | 9/2006 | Livesey et al. | |
| 2006/0272102 A1 | 12/2006 | Liu et al. | |
| 2007/0009586 A1 | 1/2007 | Cohen et al. | |
| 2007/0010897 A1 | 1/2007 | Stone | |
| 2007/0248575 A1 | 10/2007 | Connor et al. | |
| 2008/0027562 A1 | 1/2008 | Fujisato et al. | |
| 2009/0130221 A1 | 5/2009 | Bolland et al. | |
| 2009/0202977 A1 | 8/2009 | Ott et al. | |
| 2009/0239809 A1 | 9/2009 | Chen et al. | |

(Continued)

FOREIGN PATENT DOCUMENTS

| | | | | |
|---|---|---|---|---|
| CN | 1266716 A | 9/2000 | | |
| GB | 2482166 A * | 1/2012 | ........... | A61L 15/325 |

(Continued)

OTHER PUBLICATIONS

U.S. Appl. No. 14/019,274, filed Sep. 5, 2013.
U.S. Appl. No. 13/457,791, filed Apr. 27, 2012, U.S. Pat. No. 9,206,442, Dec. 8, 2015.
U.S. Appl. No. 14/478,373, filed Sep. 5, 2014.
U.S. Appl. No. 14/924,931, filed Oct. 28, 2015.
Badylak et al., "Extracellular Matrix as a Biological Scaffold Material: Structure and Function," Acta Biomaterialia, 5:1-13 (2009).

(Continued)

*Primary Examiner* — Chris R Tate
*Assistant Examiner* — Douglas F White
(74) *Attorney, Agent, or Firm* — McCarter & English, LLP

(57) ABSTRACT

Methods for treating tissue matrices and tissue matrices produced according to the methods are provided. The methods can include treating a tissue matrix with a proteolytic enzyme to produce a desired pliability of the tissue matrix and/or to control the immunogenicity of the tissue matrix. The methods can also comprise performing an assay to determine if contacting the at least one collagen-containing tissue matrix with a proteolytic enzyme has altered the at least one collagen-containing tissue matrix to reduce a human immune response to the tissue matrix.

13 Claims, 9 Drawing Sheets

(56) References Cited

U.S. PATENT DOCUMENTS

| | | |
|---|---|---|
| 2009/0306790 A1 | 12/2009 | Sun |
| 2010/0119577 A1 | 5/2010 | Min et al. |
| 2010/0179639 A1 | 7/2010 | Bloor et al. |
| 2010/0196870 A1 | 8/2010 | Stone et al. |
| 2010/0233235 A1 | 9/2010 | Matheny et al. |
| 2011/0021753 A1 | 1/2011 | Huang |
| 2012/0252065 A1 | 10/2012 | Rozenszain et al. |
| 2012/0276213 A1 | 11/2012 | Chen |
| 2013/0013068 A1 | 1/2013 | Forsell et al. |
| 2013/0028981 A1 | 1/2013 | Gratzer |

FOREIGN PATENT DOCUMENTS

| | | |
|---|---|---|
| JP | 2004-107303 A | 4/2004 |
| JP | 2004-107303 A | 4/2004 |
| JP | 52-30097 B2 | 7/2013 |
| WO | WO-1999/044533 A1 | 9/1999 |
| WO | WO-2001/091671 A1 | 12/2001 |
| WO | WO-2003/017826 A2 | 3/2003 |
| WO | WO-2003/097694 A1 | 11/2003 |
| WO | 2004/020470 A1 | 3/2004 |
| WO | WO-2004/020470 A1 | 3/2004 |
| WO | 2005/089411 A2 | 9/2005 |
| WO | 2006/095342 A2 | 9/2006 |
| WO | WO-2007/043513 A1 | 4/2007 |
| WO | WO-2008/125850 A2 | 10/2008 |
| WO | WO-2009/049568 A2 | 4/2009 |

OTHER PUBLICATIONS

Collins et al., "Cardiac Xenografts Between Primate Species Provide Evidence for the Importance of the α-Galactosyl Determinant in Hyperacute Rejection," J. Immunol. 154:5500-5510 (1995).

Dobrin et al., "Elastase, collagenase, and the biaxial elastic properties of dog carotid artery," Am. J. Physiol. Heart Circ. Physiol., 247:H124-H131 (1984).

Galili et al., "Interaction between human natural anti-alpha-galactosyl immunoglobulin G and bacteria of the human flora," Infect. Immun. 56:1730-1737 (1988).

Galili et al., "Interaction of the natural anti-Gal antibody with α-galactosyl epitopes: a major obstacle for xenotransplantation in humans," Immunology Today 14: 480-482 (1993).

Galili et al., "Man, apes, and Old World monkeys differ from other mammals in the expression of alpha-galactosyl epitopes on nucleated cells," J. Biol. Chem. 263:17755-17762 (1988).

Good et al., "Identification of Carbohydrate Structures That Bind Human Antiporcine Antibodies: Implications for Discordant Xenografting in Humans," Transplant Proc. 24: 559-562 (1992).

Hamadeh et al., "Human natural anti-Gal IgG regulates alternative complement pathway activation on bacterial surfaces," J. Clin. Invest. 89:1223-1235 (1992).

International Search Report and Written Opinion for PCT/US2012/035361 dated Jun. 28, 2012, from the International Searching Authority of the European Patent Office.

International Search Report and Written Opinion for International Patent Application No. PCT/US2009/046193, dated Jul. 30, 2010 (12 pages).

Ionescu et al., "Effect of Papain and Bromelin on Muscle and Collagen Proteins in Beef Meat," The Annals of the University Dunarea de Jos of Galati. Fascicle VI, Food Technology, New Series, pp. 9-16, 2008 [Abstract].

Karlinsky et al., "In Vitro Effects of Elastase and Collagenase on Mechanical Properties of Hamster Lungs," Chest, 69(2):275-276 (1976).

Lu et al., "Novel Porous Aortic Elastin and Collagen Scaffolds for Tissue Engineering," Biomaterials, 25(22):5227-5237 (2004).

Reihsner et al., "Biomechanical properties of elastase treated palmar aponeuroses," Connective Tissue Research, 26:77-86 (1991).

Sandrin et al., "Anti-pig IgM antibodies in human serum react predominantly with Gal(alpha 1-3)Gal epitopes," Proc. Natl. Acad. Sci. USA 90: 11391-11395 (1993).

Tedder et al., "Stabilized Collagen Scaffolds for Heart Valve Tissue Engineering," Tissue Engineering: Part A, pp. 1-12 (2008).

Xu, "A Porcine-Derived Acellular Dermal Scaffold that Supports Soft Tissue Regeneration: Removal of Terminal Galactose-α-(1,3)-Galactose and Retention of Matrix Structure," Tissue Engineering, vol. 15:1-13 (2009).

Yuan et al., "Effects of collagenase and elastase on the mechanical properties of lung tissue strips," J. App. Physiol., 89:3-14 (2000).

Parenteau-Bareil et al. "Collagen-Based Biomaterials for Tissuse Engineering Applications," Materials, 3:1863-1887 (2010).

International Preliminary Report on Patentability for corresponding International Patent Application No. PCT/US2014/054206, dated Mar. 17, 2016.

Gilbert et al. "Decellularization of tissues and organs," Biomaterials, 27:3675-3683 (2006).

Final Office Action for U.S. Appl. No. 14/478,373, dated Apr. 6, 2017, 22 pages.

Response to Final Office Action for U.S. Appl. No. 14/478,373, dated Jul. 24, 2017, 11 pages.

Non-Final Office Action for U.S. Appl. No. 14/478,373, dated Nov. 3, 2017, 23 pages.

* cited by examiner

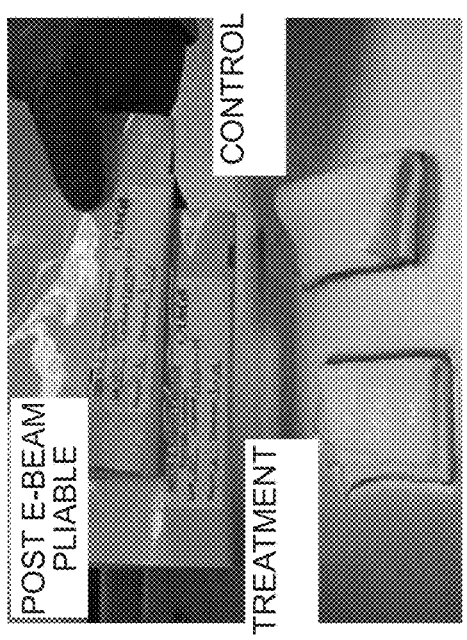
FIG. 1A
FIG. 1B
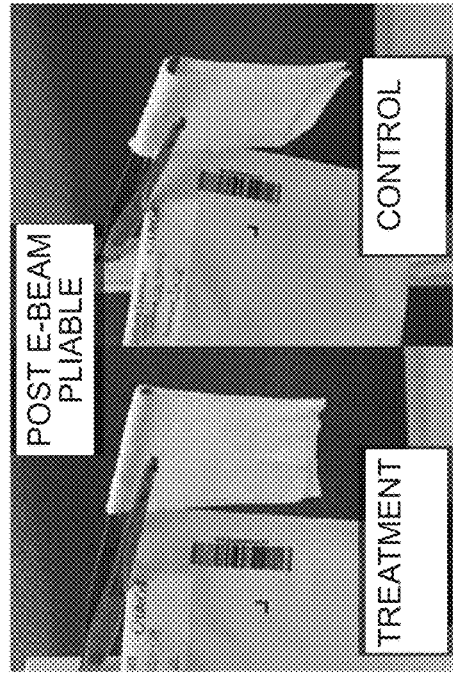
FIG. 1C
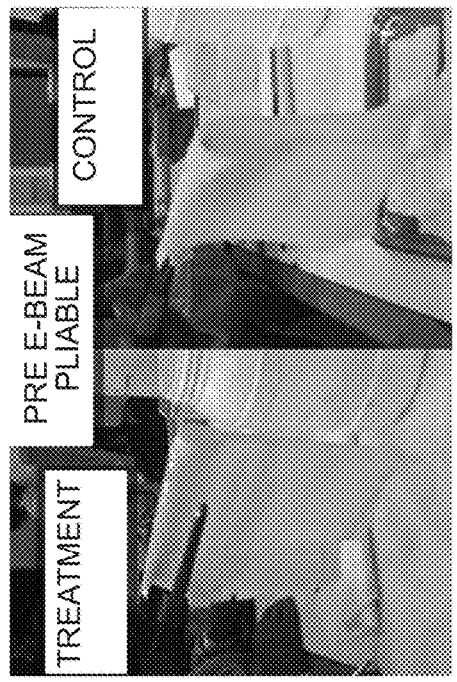
FIG. 1D

CONTROL (UNTREATED)

CONTROL (UNTREATED)

TREATED

TREATED

CONTROL (UNTREATED)

TREATED

CONTROL (UNTREATED)

CONTROL (UNTREATED)

TREATED

TREATED

METHOD FOR ENZYMATIC TREATMENT OF TISSUE PRODUCTS

This application is a continuation of U.S. application Ser. No. 14/019,274, which was filed on Sep. 5, 2013, which is a continuation-in-part under 35 U.S.C. § 120 of U.S. application Ser. No. 13/457,791, which was filed on Apr. 27, 2012, and which claims priority under 35 U.S.C. § 119 to U.S. Provisional Application No. 61/479,937, which was filed on Apr. 28, 2011.

The present disclosure relates to tissue matrices, and more particularly, to methods for controlling the pliability and/or immunogenicity of tissue matrices by treating the matrices with proteolytic enzymes.

Various tissue-derived products are used to regenerate, repair, or otherwise treat diseased or damaged tissues and organs. Such products can include intact tissue grafts and/or acellular or reconstituted acellular tissues (e.g., acellular tissue matrices from skin, intestine, or other tissues, with or without cell seeding). Such products generally have mechanical properties determined by the tissue source (i.e., tissue type and animal from which it originated) and the processing parameters used to produce the tissue products. Since tissue products are often used for surgical applications and/or tissue replacement or augmentation, the mechanical properties of the tissue products are important. For example, surgeons generally prefer tissues that feel like natural tissues and/or are easy to handle during surgical procedures. Some tissue products, however, are undesirably stiff and/or have an unnatural feel. Accordingly, methods for treating tissue products to produce more desirable mechanical properties are provided.

In addition, when implanted in the body, tissue products derived from exogenous materials (e.g., tissues from other animals or patients, as well as processed tissues of any type), may elicit an inflammatory or immune response in the recipient. In some cases, an excessive immune response may be detrimental, causing the implant to form undesirable scar tissue, or preventing suitable regeneration of tissue at the site of implantation. Accordingly, methods for treating tissue products to reduce or control the immune response of the tissue products upon implantation are provided.

SUMMARY

According to certain embodiments, a method for treating a tissue matrix is provided. The method can comprise selecting a collagen-containing tissue matrix and contacting the tissue matrix with a proteolytic enzyme under conditions sufficient to produce a desired level of pliability in the tissue matrix.

In another embodiment, a method for treating a tissue matrix is provided. The method can comprise selecting a collagen-containing acellular tissue matrix and contacting the tissue matrix with a proteolytic enzyme under conditions sufficient to produce a desired level of pliability in the tissue matrix and to increase the porosity of the tissue matrix.

In some embodiments, an acellular tissue matrix is provided. The matrix can be prepared by a process comprising selecting an acellular tissue matrix and contacting the tissue matrix with a proteolytic enzyme under conditions sufficient to produce a desired level of pliability in the tissue matrix.

According to certain embodiments, a method for treating a tissue matrix is provided. The method can include selecting at least one collagen-containing tissue matrix; contacting the at least one collagen-containing tissue matrix with a proteolytic enzyme; and performing an assay to determine if contacting the at least one collagen-containing tissue matrix with the at least one proteolytic enzyme has altered the at least one collagen-containing tissue matrix to reduce a human immune response to the tissue matrix when the tissue matrix is implanted in a human body.

DESCRIPTION OF THE DRAWINGS

FIGS. 1A through 1D show acellular tissue matrices after treatment with enzymes using methods of described in Example 1, as well as untreated controls.

DESCRIPTION OF CERTAIN EXEMPLARY EMBODIMENTS

Figure 2:
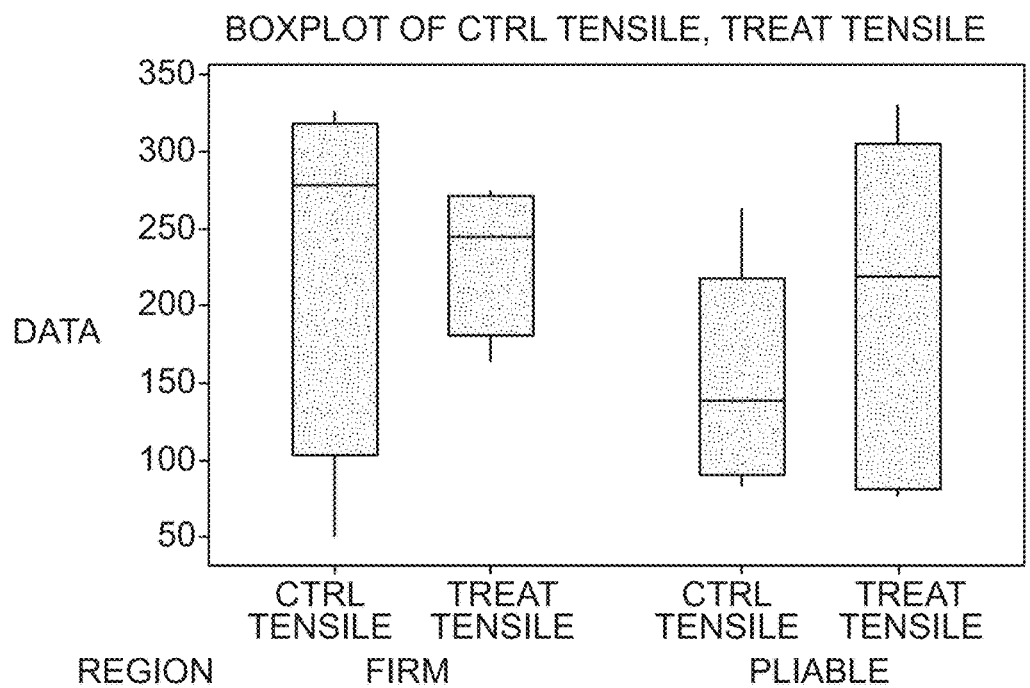
FIG. 2 is a box plot of tensile strength testing data for treated and control samples, according to the methods of Example 1.
Figure 3:
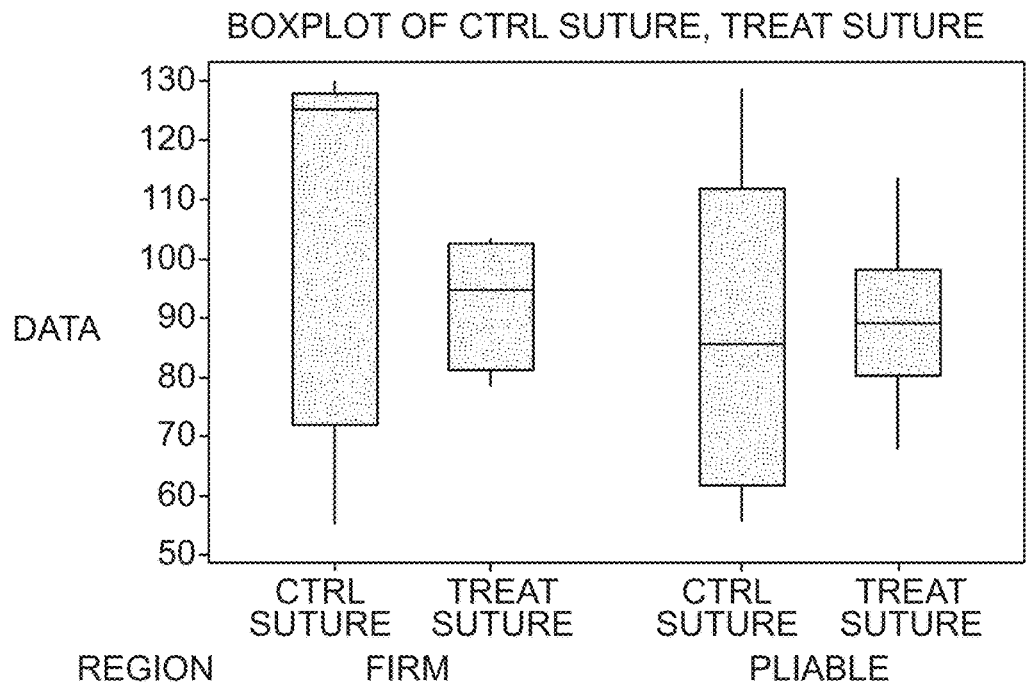
FIG. 3 is a box plot of suture strength testing data for treated and control samples, according to the methods of Example 1.
Figure 4:
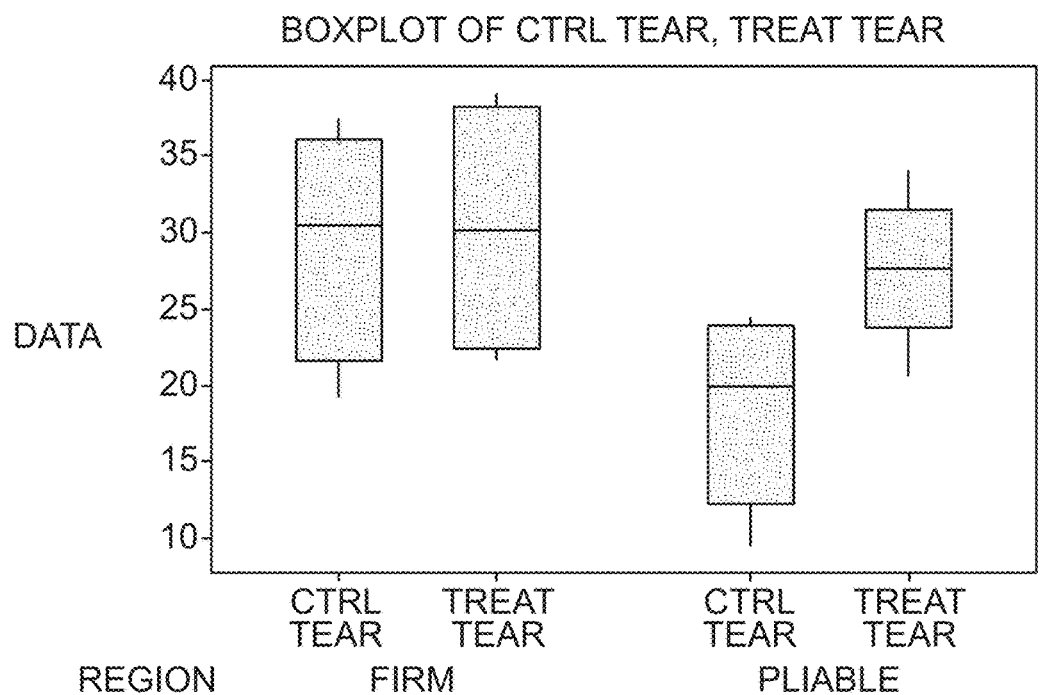
FIG. 4 is a box plot of tear strength testing data for treated and control samples, according to the methods of Example 1.
Figure 5:
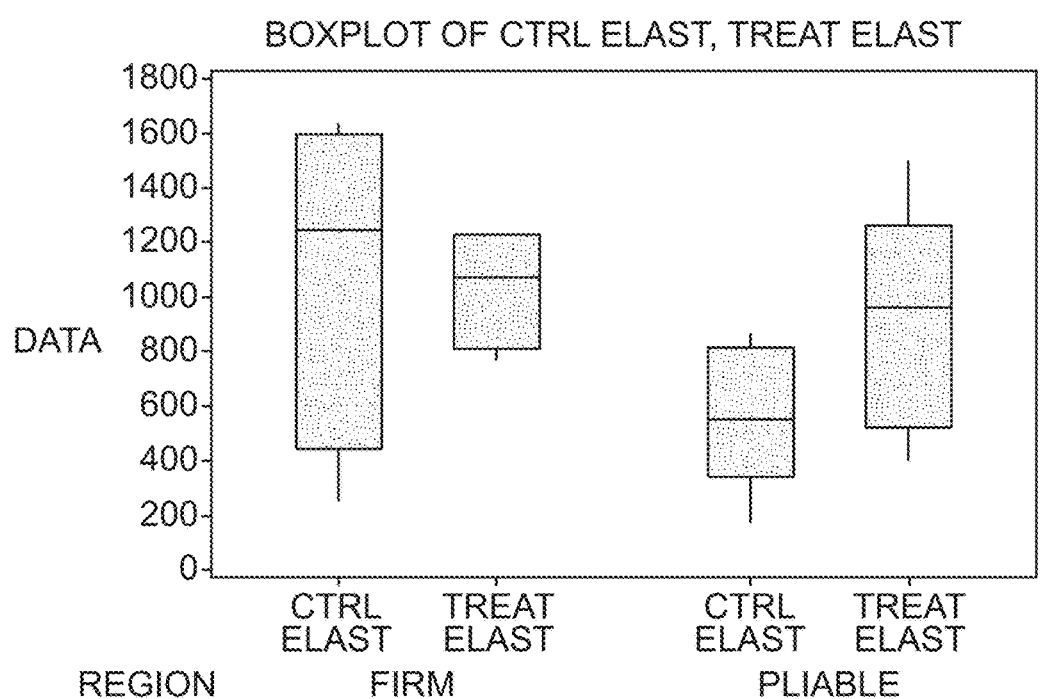
FIG. 5 is a box plot of elasticity testing data for treated and control samples, according to the methods of Example 1.
Figure 6:
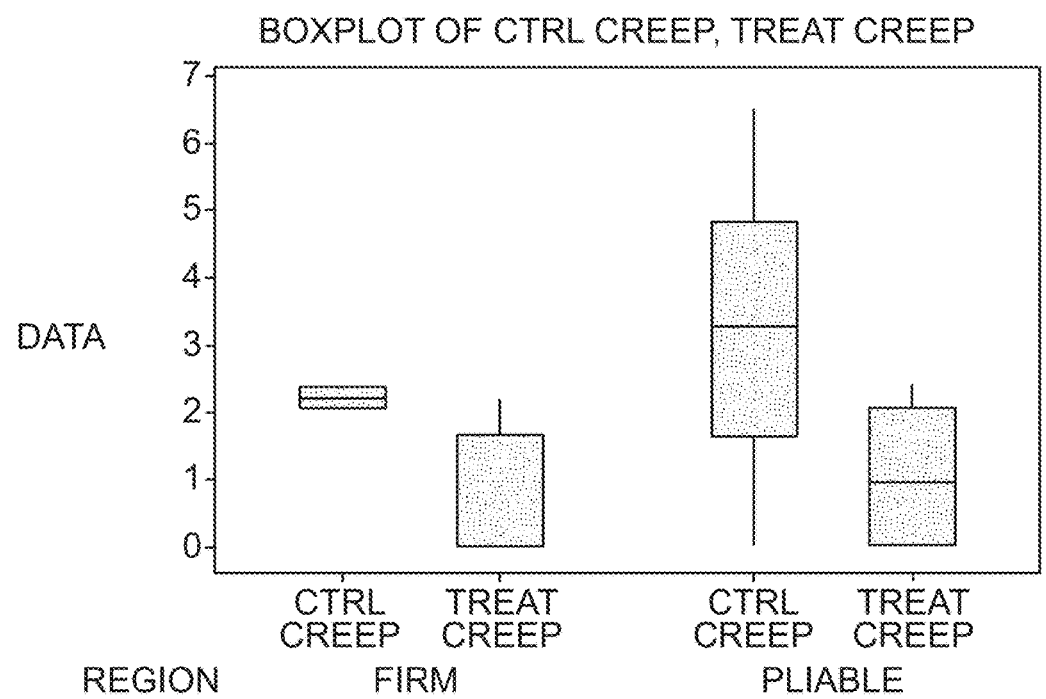
FIG. 6 is a box plot of creep resistance testing data for treated and control samples, according to the methods of Example 1.

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

As used herein "tissue product" will refer to any human or animal tissue that contains extracellular matrix proteins. "Tissue products" can include acellular or partially decellularized tissue matrices, decellularized tissue matrices that have been repopulated with exogenous cells, and/or cellular tissues.

Various human and animal tissues can be used to produce products for treating patients. For example, various tissue products for regeneration, repair, augmentation, reinforcement, and/or treatment of human tissues that have been damaged or lost due to various diseases and/or structural damage (e.g., from trauma, surgery, atrophy, and/or long-term wear and degeneration) have been produced. Such products can include, for example, acellular tissue matrices, tissue allografts or xenografts, and/or reconstituted tissues (i.e., at least partially decellularized tissues that have been seeded with cells to produce viable materials).

For surgical applications, it is often desirable to produce tissue products that have certain mechanical properties. For example, the tissue product, which may include a sheet of material, should possess sufficient strength to withstand the intended use. For example, certain tissue products may be used to repair defects (e.g., hernias), to support surrounding tissues or implants (e.g., for breast augmentation and/or reconstruction), or to replace damaged or lost tissue (e.g., after trauma or surgical resection). Whatever the particular use, the tissue product should have sufficient strength, elasticity, and/or other mechanical properties to function until tissue regeneration and/or repair occurs.

In addition, tissue products should have a desirable feel. For example, surgeons generally prefer materials that have a natural tissue-like feel (e.g., are sufficiently soft, pliable, and/or elastic). Further, after implantation, it is desirable for tissue products to feel more natural. For example, tissues used for breast augmentation should not be excessively stiff so that upon implantation they produce a more natural feeling breast.

Some tissue products, however, can be excessively stiff. For example, some surgeons note that porcine-derived dermal materials such as STRATTICE™ are less pliable than human dermal products such as ALLODERM®. Processes for improving the feel of such products, however, should not adversely affect the biological and/or mechanical properties of the products. Specifically, processing of the products to improve the feel of the products should not produce an undesirable decrease in other mechanical properties such as tensile strength, and should not alter the protein matrix in such a way that the material does not support tissue regeneration and/or repair.

The present disclosure provides methods for treating tissues to improve the feel of tissue products produced from the tissues. The disclosure also provides tissue products produced using the methods of treatment. In addition, the present disclosure provides methods of treating tissues to control the porosity of tissue products produced from the tissues. In some cases, controlling the porosity can improve cellular infiltration and tissue regeneration and/or repair.

In addition, the present disclosure provides methods for controlling or reducing an immune response to tissue matrices when implanted in a body. The immune response can be measured using a number of immunoassays, including monocyte activation assays, phagocytosis assays, and/or oxidative burst assays. The immunogenicity may also be controlled while treating the tissue to improve the feel of the tissue, to control mechanical properties of the tissue (including any mechanical property listed herein), and/or controlling porosity of the tissue. After treatment of the tissue matrices, the matrices may be subjected to an assay to determine if the immunogenicity of the tissue has been altered in a desirable way.

Accordingly, in one embodiment, a method for treating a tissue matrix is provided. The method can comprise selecting a collagen-containing tissue matrix and contacting the tissue matrix with a proteolytic enzyme under conditions sufficient to produce a desired level of pliability in the tissue matrix. In another embodiment, a method for treating a tissue matrix is provided. The method can comprise selecting a collagen-containing acellular tissue matrix and contacting the tissue matrix with a proteolytic enzyme under conditions sufficient to produce a desired level of pliability in the tissue matrix and to increase the porosity of the tissue matrix. FIGS. 1A-1D show acellular tissue matrices (STRATTICE™) after treatment with enzymes using methods of the present disclosure, as well as untreated controls. As shown, the treated samples are significantly more pliable that the untreated samples.

According to certain embodiments, a method for treating a tissue matrix is provided. The method can include selecting at least one collagen-containing tissue matrix; contacting the at least one collagen-containing tissue matrix with a proteolytic enzyme; and performing an assay to determine if contacting the at least one collagen-containing tissue matrix with the at least one proteolytic enzyme has altered the at least one collagen-containing tissue matrix to reduce a human immune response to the tissue matrix when the tissue matrix is implanted in a human body.

In various embodiments, treatment of tissue matrices with proteolytic enzymes provides improved mechanical properties without causing degradation in one or biological properties. For example, treatment of tissue matrices can produce desired stiffness, feel, tactile properties, and/or desired porosity without causing increased inflammation or scar formation and/or without causing a reduction in the tissue matrices' ability to promote cell ingrowth and regeneration.

The tissues can be selected to provide a variety of different biological and mechanical properties. For example, an acellular tissue matrix or other tissue product can be selected to allow tissue in-growth and remodeling to assist in regeneration of tissue normally found at the site where the matrix is implanted. For example, an acellular tissue matrix, when implanted on or into fascia, may be selected to allow regeneration of the fascia without excessive fibrosis or scar formation. In certain embodiments, the tissue product can be formed from ALLODERM® or STRATTICE™, which are human and porcine acellular dermal matrices respectively. Alternatively, other suitable acellular tissue matrices can be used, as described further below. The tissues can be selected from a variety of tissue sources including skin (dermis or whole skin), fascia, pericardial tissue, dura, umbilical cord tissue, placental tissue, cardiac valve tissue, ligament tissue, adipose tissue, tendon tissue, arterial tissue, venous tissue, neural connective tissue, urinary bladder tissue, ureter tissue, and intestinal tissue. The methods described herein can be used to process any collagenous tissue type, and for any tissue matrix product. For example, a number of biological scaffold materials are described by Badylak et al., and the methods of the present disclosure can be used to treat those or other tissue products known in the art. Badylak et al., "Extracellular Matrix as a Biological Scaffold Material: Structure and Function," *Acta Biomaterialia* (2008), doi: 10.1016/j.actbio.2008.09.013.

In some cases, the tissue product can be provided as a decellularized tissue matrix. Suitable acellular tissue matrices are described further below. In other cases, the method can further include processing intact tissue to remove cells or other materials. The tissues can be completely or partially decellularized to yield acellular tissue matrices or extracellular tissue materials to be used for patients. For example, various tissues, such as skin, intestine, bone, cartilage, adipose tissue, nerve tissue (e.g., nerve fibers or dura), tendons, ligaments, or other tissues can be completely or partially decellularized to produce tissue products useful for patients. In some cases, these decellularized products can be used without addition of exogenous cellular materials (e.g., stem cells). In certain cases, these decellularized products can be seeded with cells from autologous sources or other sources to facilitate treatment. Suitable processes for producing acellular tissue matrices are described below.

A number of different enzymes can be used to treat the tissue matrices. For example, suitable enzymes can include sulfhydryl proteases such as bromelain. In addition, they can include bromelain, papain, ficin, actinidin, alcalase, trypsin or combinations thereof. The enzymes can be purchased commercially or extracted from fruit sources. For example, one source of bromelain is MCCORMICK MEAT TENDERIZER®, but the enzymes can also be extracted from pineapple and/or purchased in a medical-grade formulation.

The enzymes can be contacted with the tissues to increase the pliability of the tissue without causing undesirable degradation in other mechanical and/or biological properties. For example, when a batch of materials are produced with or without the enzyme treatments discussed herein, the enzyme treatments will not produce an undesirable change in at least one of tensile strength, tear strength, suture strength, creep resistance, elasticity, collagenase susceptibility, glycosaminoglycan content, lectin content, burst strength, thermal transition temperature, or combinations thereof. In some cases, an undesirable change is a statistically significant reduction in any one of tensile strength, tear strength, suture strength, creep resistance, glycosaminoglycan content, lectin content, burst strength, an increase in collagenase susceptibility or a change (upward or downward) in thermal transition temperature (as measured using differential scanning calorimetry).

As noted above, in some embodiments, the tissues are treated with an enzyme to increase the porosity of the tissue. In various embodiments, increasing the porosity of the tissue is performed to increase the number and/or size of channels, which can improve the rate of cellular infiltration and tissue regeneration.

In some cases, the enzymes are selected such that they cause site-specific cleavage of proteins within the tissues. For example, it has been found that treatment of porcine dermal materials with bromelain does not cause further alterations in the matrix structure after a certain amount of treatment. Therefore, treatment of dermis with bromelain does not cause further change in the matrix with prolonged exposure or after extended periods of time.

In addition, the enzyme can be applied to the tissues in a variety of suitable solutions. For example, bromelain has been found to be effective when applied to tissues in normal saline, but other suitable buffers (e.g., PBS) can be used.

As noted above, after treatment with an enzyme, an assay may be performed to determine if contacting the at least one collagen-containing tissue matrix with the at least one proteolytic enzyme has altered the at least one collagen-containing tissue matrix to reduce a human immune response to the tissue matrix when the tissue matrix is implanted in a human body. A number of suitable assays may be performed. For example, suitable assays can include monocyte activation assays, phagocytosis assays, and oxidative burst assays.

In some embodiments, the assay may be performed on a segment or portion of the processed tissue, and other portions of the tissue may be used in subsequent medical or surgical procedures. In other embodiments, the assay may be performed on one or more samples from a batch of multiple samples, and samples not subjected to the assay may be subsequently selected for use in treating a patient.

In certain embodiments, the enzyme treatment is selected to remove collagen or other proteins in the material that have a thermal transition temperature that will permit denaturation at body temperature. For example, in some embodiments, dermal acellular tissues are selected, and the enzymatic treatment is selected to remove a thermal peak, as measured using DSC, between about 30 degrees and 40 degrees Celsius. This small ECM peak is expected to denature spontaneously at the human body temperature and may contribute to the different inflammatory Acellular Tissue Matrices The term "acellular tissue matrix," as used herein, refers generally to any tissue matrix that is substantially free of cells and/or cellular components. Skin, parts of skin (e.g., dermis), and other tissues such as blood vessels, heart valves, fascia, cartilage, adipose tissue, bone, and nerve connective tissue may be used to create acellular matrices within the scope of the present disclosure. Acellular tissue matrices can be tested or evaluated to determine if they are substantially free of cell and/or cellular components in a number of ways. For example, processed tissues can be inspected with light microscopy to determine if cells (live or dead) and/or cellular components remain. In addition, certain assays can be used to identify the presence of cells or cellular components. For example, DNA or other nucleic acid assays can be used to quantify remaining nuclear materials within the tissue matrices. Generally, the absence of remaining DNA or other nucleic acids will be indicative of complete decellularization (i.e., removal of cells and/or cellular components). Finally, other assays that identify cell-specific components (e.g., surface antigens) can be used to determine if the tissue matrices are acellular. Skin, parts of skin (e.g., dermis), and other tissues such as blood vessels, heart valves, fascia, cartilage, bone, and nerve connective tissue may be used to create acellular matrices within the scope of the present disclosure.

In general, the steps involved in the production of an acellular tissue matrix include harvesting the tissue from a donor (e.g., a human cadaver or animal source) and cell removal under conditions that preserve biological and structural function. In certain embodiments, the process includes chemical treatment to stabilize the tissue and avoid biochemical and structural degradation together with or before cell removal. In various embodiments, the stabilizing solution arrests and prevents osmotic, hypoxic, autolytic, and proteolytic degradation, protects against microbial contamination, and reduces mechanical damage that can occur with tissues that contain, for example, smooth muscle components (e.g., blood vessels). The stabilizing solution may contain an appropriate buffer, one or more antioxidants, one or more oncotic agents, one or more antibiotics, one or more protease inhibitors, and/or one or more smooth muscle relaxants.

The tissue is then placed in a decellularization solution to remove viable cells (e.g., epithelial cells, endothelial cells, smooth muscle cells, and fibroblasts) from the structural matrix without damaging the biological and structural integrity of the collagen matrix. The decellularization solution may contain an appropriate buffer, salt, an antibiotic, one or more detergents (e.g., TRITON X-100™, sodium deoxycholate, polyoxyethylene (20) sorbitan mono-oleate), one or more agents to prevent cross-linking, one or more protease inhibitors, and/or one or more enzymes. In some embodiments, the decellularization solution comprises 1% TRITON X-100™ in RPMI media with Gentamicin and 25 mM EDTA (ethylenediaminetetraacetic acid). In some embodiments, the tissue is incubated in the decellularization solution overnight at 37° C. with gentle shaking at 90 rpm. In certain embodiments, additional detergents may be used to remove fat from the tissue sample. For example, in some embodiments, 2% sodium deoxycholate is added to the decellularization solution.

After the decellularization process, the tissue sample is washed thoroughly with saline. In some exemplary embodiments, e.g., when xenogenic material is used, the decellularized tissue is then treated overnight at room temperature with a deoxyribonuclease (DNase) solution. In some embodiments, the tissue sample is treated with a DNase solution prepared in DNase buffer (20 mM HEPES (4-(2-hydroxyethyl)-1-piperazineethanesulfonic acid), 20 mM $CaCl_2$ and 20 mM $MgCl_2$). Optionally, an antibiotic solution (e.g., Gentamicin) may be added to the DNase solution. Any suitable buffer can be used as long as the buffer provides suitable DNase activity.

While an acellular tissue matrix may be made from one or more individuals of the same species as the recipient of the acellular tissue matrix graft, this is not necessarily the case. Thus, for example, an acellular tissue matrix may be made from porcine tissue and implanted in a human patient. Species that can serve as recipients of acellular tissue matrix and donors of tissues or organs for the production of the acellular tissue matrix include, without limitation, mammals, such as humans, nonhuman primates (e.g., monkeys, baboons, or chimpanzees), pigs, cows, horses, goats, sheep, dogs, cats, rabbits, guinea pigs, gerbils, hamsters, rats, or mice.

Elimination of the α-gal epitopes from the collagen-containing material may diminish the immune response against the collagen-containing material. The α-gal epitope is expressed in non-primate mammals and in New World monkeys (monkeys of South America) as well as on macromolecules such as proteoglycans of the extracellular components. U. Galili et al., J. Biol. Chem. 263: 17755 (1988). This epitope is absent in Old World primates (monkeys of Asia and Africa and apes) and humans, however. Id. Anti-gal antibodies are produced in humans and primates as a result of an immune response to α-gal epitope carbohydrate structures on gastrointestinal bacteria. U. Galili et al., Infect. Immun. 56: 1730 (1988); R. M. Hamadeh et al., J. Clin. Invest. 89: 1223 (1992).

Since non-primate mammals (e.g., pigs) produce α-gal epitopes, xenotransplantation of collagen-containing material from these mammals into primates often results in rejection because of primate anti-Gal antibody binding to these epitopes on the collagen-containing material. The binding results in the destruction of the collagen-containing material by complement fixation and by antibody dependent cell cytotoxicity. U. Galili et al., Immunology Today 14: 480 (1993); M. Sandrin et al., Proc. Natl. Acad. Sci. USA 90: 11391 (1993); H. Good et al., Transplant. Proc. 24: 559 (1992); B. H. Collins et al., J. Immunol. 154: 5500 (1995). Furthermore, xenotransplantation results in major activation of the immune system to produce increased amounts of high affinity anti-gal antibodies. Accordingly, in some embodiments, when animals that produce α-gal epitopes are used as the tissue source, the substantial elimination of α-gal epitopes from cells and from extracellular components of the collagen-containing material, and the prevention of re-expression of cellular α-gal epitopes can diminish the immune response against the collagen-containing material associated with anti-gal antibody binding to α-gal epitopes.

To remove α-gal epitopes, after washing the tissue thoroughly with saline to remove the DNase solution, the tissue sample may be subjected to one or more enzymatic treatments to remove certain immunogenic antigens, if present in the sample. In some embodiments, the tissue sample may be treated with an α-galactosidase enzyme to eliminate α-gal epitopes if present in the tissue. In some embodiments, the tissue sample is treated with α-galactosidase at a concentration of 300 U/L prepared in 100 mM phosphate buffer at pH 6.0. In other embodiments, the concentration of α-galactosidase is increased to 400 U/L for adequate removal of the α-gal epitopes from the harvested tissue. Any suitable enzyme concentration and buffer can be used as long as it is sufficient removal of antigens is achieved.

Alternatively, rather than treating the tissue with enzymes, animals that have been genetically modified to lack one or more antigenic epitopes may be selected as the tissue source. For example, animals (e.g., pigs) that have been genetically engineered to lack the terminal α-galactose moiety can be selected as the tissue source. For descriptions of appropriate animals see co-pending U.S. application Ser. No. 10/896,594 and U.S. Pat. No. 6,166,288, the disclosures of which are incorporated herein by reference in their entirety. In addition, certain exemplary methods of processing tissues to produce acellular matrices with or without reduced amounts of or lacking alpha-1,3-galactose moieties are described in Xu, Hui. et al., "A Porcine-Derived Acellular Dermal Scaffold that Supports Soft Tissue Regeneration: Removal of Terminal Galactose-α-(1,3)-Galactose and Retention of Matrix Structure," Tissue Engineering, Vol. 15, 1-13 (2009), which is incorporated by reference in its entirety.

After the acellular tissue matrix is formed, histocompatible, viable cells may optionally be seeded in the acellular tissue matrix to produce a graft that may be further remodeled by the host. In some embodiments, histocompatible viable cells may be added to the matrices by standard in vitro cell co-culturing techniques prior to transplantation, or by in vivo repopulation following transplantation. In vivo repopulation can be by the recipient's own cells migrating into the acellular tissue matrix or by infusing or injecting cells obtained from the recipient or histocompatible cells from another donor into the acellular tissue matrix in situ. Various cell types can be used, including embryonic stem cells, adult stem cells (e.g. mesenchymal stem cells), and/or neuronal cells. In various embodiments, the cells can be directly applied to the inner portion of the acellular tissue matrix just before or after implantation. In certain embodiments, the cells can be placed within the acellular tissue matrix to be implanted, and cultured prior to implantation.

EXAMPLE 1

Treatment of Tissue Matrices to Increase Pliability

The following example illustrates a process for treating materials comprising porcine dermal acellular tissue matrices with bromelain to increase the pliability of the material. As discussed below, the treatment did not cause an undesirable change in various mechanical properties. In addition, the treatment increases the porosity of the material, which may improve the rate of cellular infiltration and tissue regeneration.

For this experiment, STRATTICE™ acellular tissue matrices, as obtained from LIFECELL CORPORATION (Branchburg, N.J.) were used. STRATTICE™ is available in a pliable form and a more firm version, depending on the anatomic location of the pig from which the material was obtained. Both types were used for this experiment. The samples used for testing were cut into quarters, and three quarters were treated. Untreated samples (1 quarter) were used as controls. The controls were refrigerated during treatment. STRATTICE™ is packaged in a solution, and therefore, does not require rehydration. The treated samples were placed in 0.5 liters of cold tap water containing 55 g of MCCORMICK MEAT TENDERIZER.

FIGS. 1A-1D show acellular tissue matrices after treatment with enzymes using methods of the present disclosure, as well as untreated controls. FIGS. 2-6 are box plots of tensile strengths, suture strengths, tear strengths, elasticity, and creep resistance for each treated and control samples. The treated samples had a noticeably increased pliability compared to controls, but did not have significant reduction in other mechanical properties. In addition, no significant change in thermal transition temperature or collagenase susceptibility was found. Overall paired T-Test showed no statistical difference between control and treatment groups.

EXAMPLE 2

Treatment of Tissue Matrices to Modulate Immune Response Upon Implantation

1. Preparation of Porcine Acellular Dermal Matrix (pADM)

Porcine skin was collected from an abattoir and split to 1.3 mm by physically removing the epidermis and subcutaneous fat. The remaining dermal tissue was de-contaminated at 37° C. in PBS containing antibiotics for 24 hours.

Following de-contamination, the tissue was processed under aseptic conditions. The dermal tissue was decellularized for 24 hours with detergents to remove viable cells, washed with saline, and treated with DNAse/α-galactosidase or another 24 hours. Cellular debris and residual chemicals were removed by washing in PBS. The resulting porcine acellular dermal matrix (pADM) was stored at ambient temperature until use.

2. Preparation of Enzyme-Treated pADM pADM was treated with one of two protease enzymes (alcalase or bromelain) overnight at 37° C. Bromelain, at a concentration of 100 units/liter, was used to treat pADM either before the decellularization or after the DNAse/α-galactosidase step. Alcalase was used at a concentration of 0.1% to treat pADM before the decellularization step. Similar in vivo and in vitro results were obtained regardless of the enzymes used or the process step at which they were introduced.

3. Differential Scanning Calorimetry of Treated Samples

Figure 7:
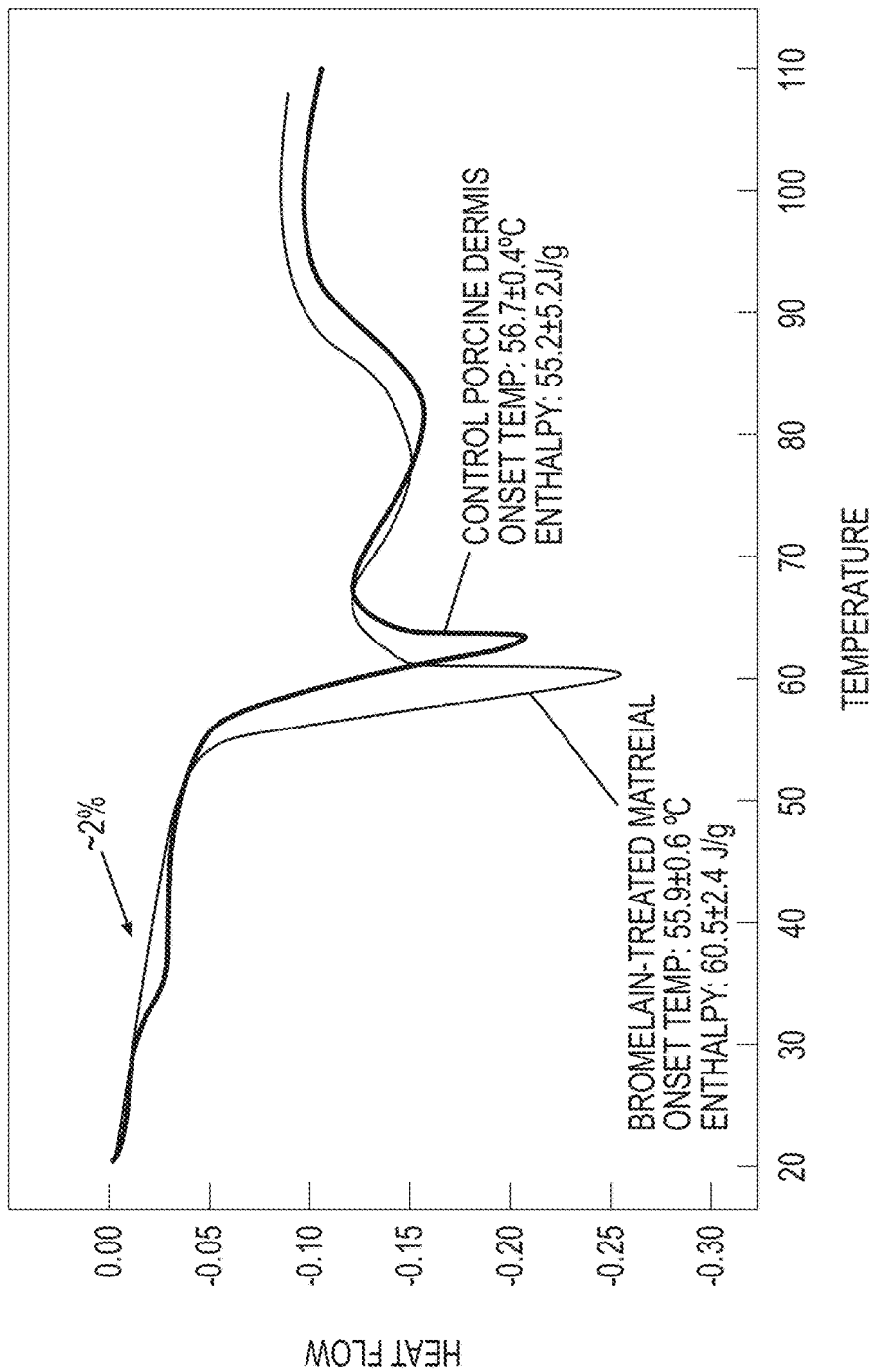
FIG. 7 illustrates DSC thermograms for untreated tissues and tissues treated using bromelain and alcalase according to Example 2.2.

The effect of bromelain enzyme treatment on porcine tissue ECM was evaluated using differential scanning calorimetric (DSC) analysis. Tissue samples were hermetically sealed and scanned at 3° C./min from 2° C. to 120° C. DSC thermograms for untreated tissues and tissues treated using the enzymes (bromelain and alcalase) according to Example 2.2 are shown in FIG. 7. The thermograms demonstrated a few alterations in the tissue ECM after enzyme treatment. First, in contrast to decellularized, untreated control tissue, the enzyme-treated ECM did not show the small peak (~2%) between 30° C. and 40° C. This small ECM peak is expected to denature spontaneously at the human body temperature and may contribute to different inflammatory responses elicited by untreated and enzyme treated pADM. Second, the two major ECM peaks above 55° C. were depressed slightly by 0.9° C. on average, possibly due to the breaking of a few inter-molecular cross links by enzymes. Third, the overall ECM denaturation enthalpy was increased by ~7.5% on average after enzyme treatment because enzyme treatment eliminated some partially unfolded collagen and some non-collagenous elements in the decellularized tissue ECM.

4. In Vitro Monocyte Activation

Monocytes are white blood cells that form part of the innate immune system. In response to inflammatory agents, they are rapidly activated and initiate an inflammatory response. To predict human inflammatory responses to enzyme-treated and untreated tissues, monocytes were isolated from human peripheral blood and incubated with the tissues overnight. Following incubation, cells were washed and stained with antibodies against two surface markers used to monitor activation, CD14 and CD163.

Figure 8B:
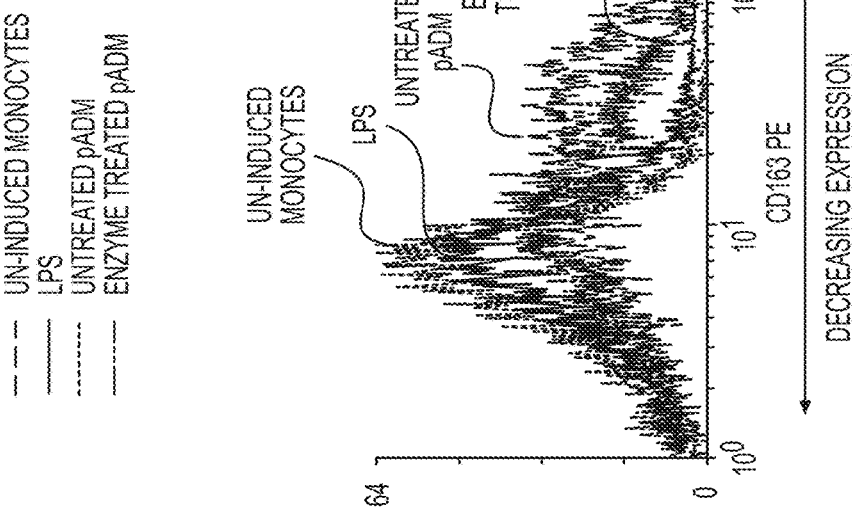
FIGS. 8A and 8B illustrate expression patterns of activation markers CD14 (A) and CD163 (B) in monocytes co-cultured with various tissues, using the monocyte activation assay described in Example 2.4.
Figure 8A:
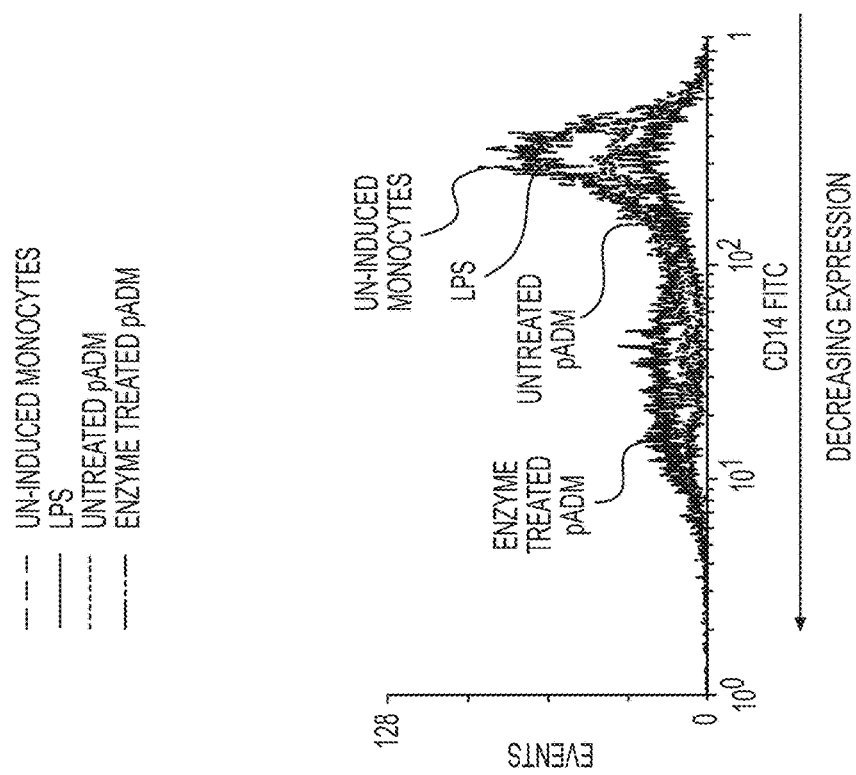
Figure 9A:
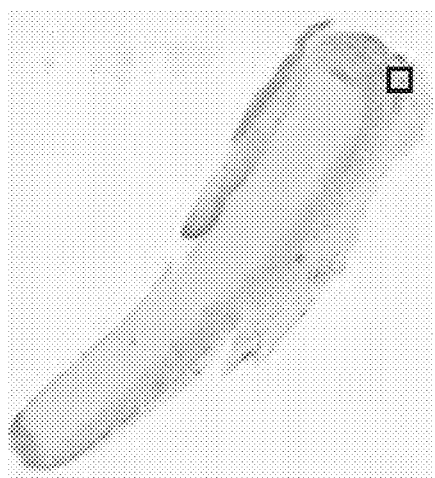
FIGS. 9A, 9B, 9D, 9E, 9C and 9F are hematoxylin & eosin (H&E) sections of untreated pADM (9A-9C) and enzyme treated pADM (9D-9F) after explant, as described in Example 2.5.
Figure 9B:
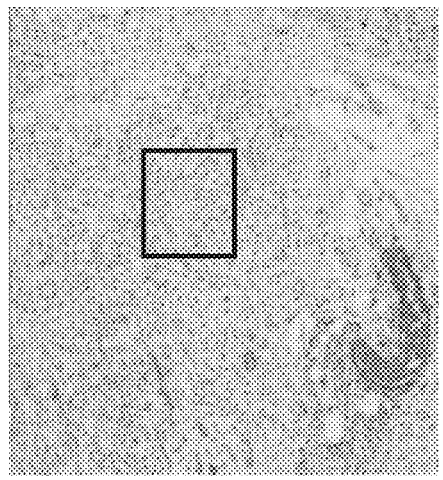
Figure 9D:
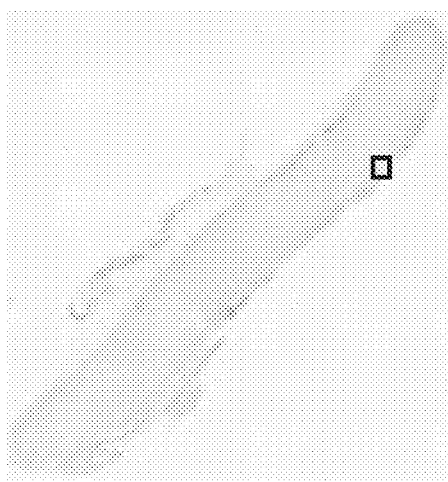
Figure 9E:
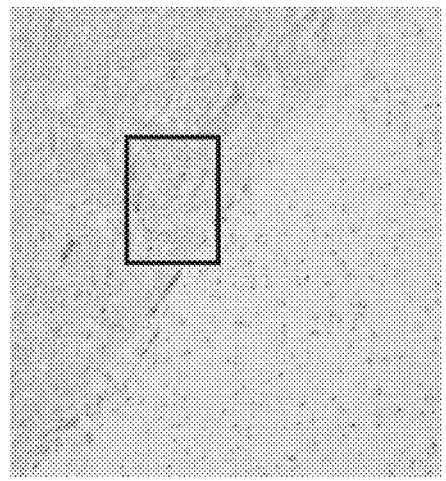
Figure 9C:
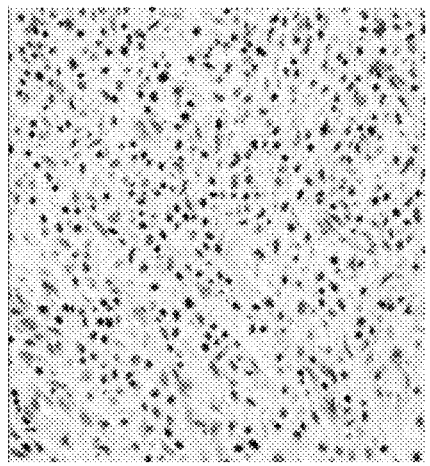
Figure 9F:
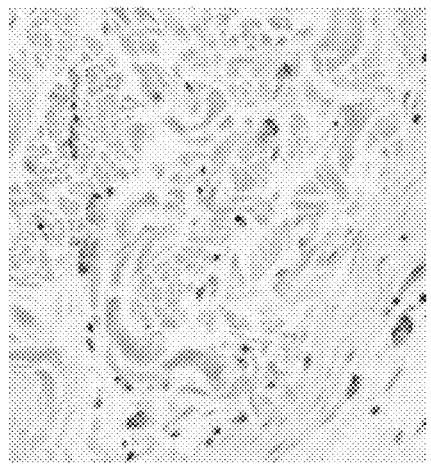
Figure 10A:
FIGS. 10A through 10D are H&E sections of untreated pADM (9A-9B) and enzyme treated pADM (9C-9D) explants, as describe in Example 2.5.
Figure 10B:
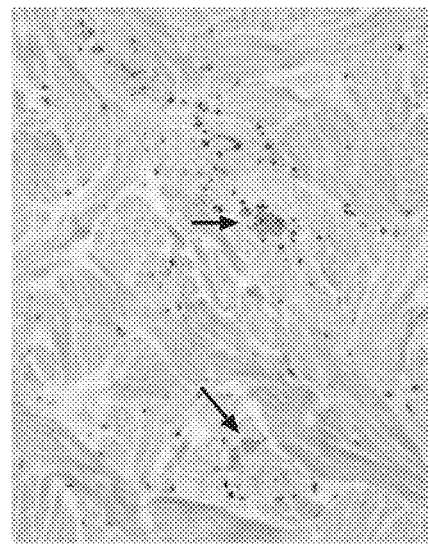
Figure 10C:
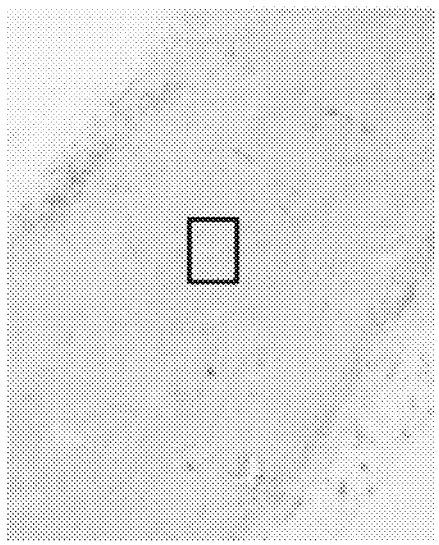
Figure 10D:
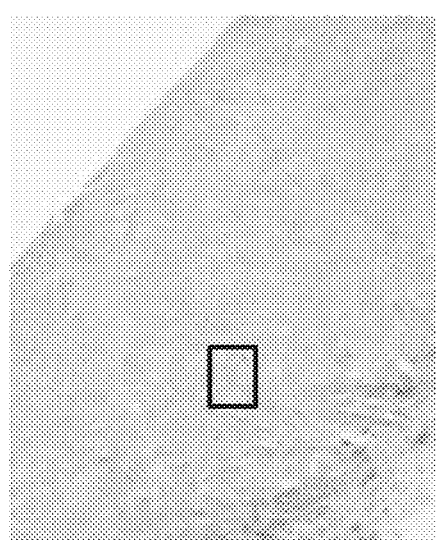

Upon activation, monocytes decrease expression of both CD14 and CD163 on their surfaces. This expression pattern was confirmed using lipopolysaccharide (LPS), a known activator of monocytes. FIGS. 8A-8B illustrate expression patterns of activation markers CD14 (A) and CD163 (B) in monocytes co-cultured with various tissues. The expression levels of CD14 and CD163 in un-induced monocytes (black) serve as baseline negative controls. For comparison, the expression patterns of these markers in un-induced monocytes served as negative controls. Enzyme-treated pADM induced a much lower level of activation than untreated pADM, as evidenced by the expression pattern of both markers. In fact, the pattern and level of CD14 expression in monocytes exposed to enzyme-treated pADM are very similar to those of un-induced monocytes. Monocytes exposed to enzyme-treated pADM had slightly decrease expression of CD163 but to a much lesser extent than monocytes exposed to either untreated pADM or LPS.

The results indicate that enzyme-treated pADM induces minimal inflammatory responses in human monocytes. Upon monocyte activation, expressions of both CD14 and CD163 decrease. This pattern is confirmed by cells co-cultured with a known monocyte activator, lipopolysaccharide (LPS). Untreated pADM (red) show lower expressions of CD14 and CD163 compared to enzyme-treated pADM (green), indicating enzyme treatment decreases monocyte activation. Thus, enzyme-treated pADM elicit less of an inflammatory response in human monocytes.

5. In Vivo Performance of pADM and Enzyme-Treated pADM

To assess the in vivo performance of pADM and enzyme-treated pADM, 1 cm×1 cm pieces of pADM and enzyme treated pADM were implanted in subcutaneous tissue of immune competent rats. At two and four weeks after implantation, the tissues were explanted and processed for histological evaluation of inflammation, cellular repopulation, and revascularization.

FIGS. 9A-F are hematoxylin & eosin (H&E) sections of untreated pADM (9A-9C) and enzyme treated pADM (9D-9F) after explant, as described in above. FIGS. 10A-D are H&E section of untreated pADM (9A-9B) and enzyme treated pADM (C-D) explants, as described above. Enzyme treated pADM induced minimal to no inflammation, while untreated pADM induced moderate to high inflammatory responses characterized by the presence of abundant of immune cells. Furthermore, enzyme-treated pADM explants exhibited enhanced cellular repopulation and revascularization compared to untreated pADM. In the untreated pADM, fibroblast-like cells and vascular structures were present mainly on the periphery of the tissue. In contrast, those same cells and vascular structures were observed throughout the enzyme treated pADM, including in the middle of the tissue.

6. Collagenase Digestion Assays

Different aliquots of freeze-dried pADMs and enzyme-treated (using bromelain, trypsin, and alcalase) pADMs were weighed and digested with collagenase Type I for varying lengths of time. At each timepoint, some aliquots of digested samples were separated from the collagenase I solution by centrifugation and washed with water to remove residual collagenase I solution. All aliquots were again freeze dried and weighed. The percentage of matrix remaining at each timepoint was calculated by taking the ratio of the dry weight of the digested sample to the dry weight of the initial sample.

Enzyme treatment did not negatively impact the susceptibility of pADMs to collagenase digestion. Both pADMs and enzyme treated pADMs were digested by collagenase Type I to the same degree and at the same rate. Accordingly, the methods of the present disclosure have been found to provide improved immunological properties upon implantation without causing a degradation in collagenase susceptibility.

What is claimed is:

1. A method for treating a tissue matrix, comprising:
selecting at least one collagen-containing tissue matrix;
contacting the at least one collagen-containing tissue matrix with a first solution comprising a proteolytic enzyme to create an enzyme-treated tissue matrix; and
treating the enzyme-treated tissue matrix with a second solution to remove at least some of the cells and cellular components from the enzyme-treated tissue matrix,
wherein the enzyme comprises alcalase and is contacted with the tissue matrix under conditions sufficient to produce a desired level of pliability in the tissue matrix and to produce a desired increase in porosity of the tissue matrix and reduce an immunogenicity of the tissue matrix when implanted in a human recipient.

2. The method of claim 1, wherein the tissue matrix treatment with the second solution is performed under conditions that produce an acellular tissue matrix.

3. The method of claim 1, wherein the tissue matrix is obtained from a tissue selected from fascia, pericardial tissue, dura, umbilical cord tissue, placental tissue, cardiac valve tissue, ligament tissue, tendon tissue, arterial tissue, venous tissue, neural connective tissue, urinary bladder tissue, ureter tissue, and intestinal tissue.

4. The method of claim 1, wherein the tissue matrix is contacted with the first solution comprising the proteolytic enzyme under conditions that do not produce an undesirable change in at least one of tensile strength, tear strength, suture strength, creep resistance, burst strength, thermal transition temperature, collagenase susceptibility or combinations thereof.

5. The method of claim 1, wherein the tissue matrix is contacted with the first solution comprising the proteolytic enzyme under conditions that do not cause a statistically significant change in tensile strength, tear strength, suture strength, creep resistance, thermal transition temperature, collagenase susceptibility or combinations thereof.

6. The method of claim 1, wherein the second solution includes a detergent.

7. The method of claim 1, including removal of all the cells and cellular components from the enzyme-treated tissue matrix.

8. The method of claim 1, further comprising performing a monocyte activation assay on the enzyme-treated tissue matrix.

9. The method of claim 1, wherein the at least one collagen-containing tissue matrix includes two or more tissue matrices.

10. The method of claim 1, further comprising packaging the tissue matrix.

11. The method of claim 1, further comprising sterilizing the tissue matrix.

12. The method of claim 1, wherein the tissue matrix comprises a dermal tissue matrix.

13. The method of claim 12, wherein the dermal tissue matrix does not contain an epidermis.

* * * * *